US009238085B2

(12) United States Patent
Lee et al.

(10) Patent No.: US 9,238,085 B2
(45) Date of Patent: Jan. 19, 2016

(54) METERING DEVICE

(75) Inventors: Hyeck-Hee Lee, St. Ingbert (DE); Ute Steinfeld, St. Ingbert (DE); Chang-Ho Kim, Seoul (KR); Jungtae Kim, Saarbrucken (DE); Holger Krause, Neunkirchen (DE)

(73) Assignees: KIST-Europe Forschungsgesellschaft mbH (DE); F. Holzer GmbH (DE)

( * ) Notice: Subject to any disclaimer, the term of this patent is extended or adjusted under 35 U.S.C. 154(b) by 1124 days.

(21) Appl. No.: 12/864,282

(22) PCT Filed: Mar. 4, 2009

(86) PCT No.: PCT/EP2009/001528
§ 371 (c)(1),
(2), (4) Date: Nov. 18, 2010

(87) PCT Pub. No.: WO2009/109370
PCT Pub. Date: Sep. 11, 2009

(65) Prior Publication Data
US 2011/0056993 A1 Mar. 10, 2011

(30) Foreign Application Priority Data

Mar. 4, 2008 (DE) .......................... 10 2008 012 468
Jun. 12, 2008 (DE) .......................... 10 2008 027 987

(51) Int. Cl.
| G01F 11/00 | (2006.01) |
| A61L 2/238 | (2006.01) |
| B05B 11/00 | (2006.01) |

(52) U.S. Cl.
CPC .............. *A61L 2/238* (2013.01); *B05B 11/0016* (2013.01); *B05B 11/0021* (2013.01);
(Continued)

(58) Field of Classification Search
CPC ....... A61L 2/22; A61L 2/238; B05B 11/0016;
B05B 11/0021; B05B 11/0024; B05B 11/0043; B05B 11/0048; B05B 11/0062; B05B 11/0064; B05B 11/0072; B05B 11/3015; B05B 11/3022; B05B 11/3074; B05B 11/3077
USPC ................ 222/256, 340, 321.6, 321.7, 321.9, 222/321.8, 321.1, 321.2, 321.3, 321.4, 222/321.5, 385, 380, 341, 376, 382, 372, 222/189.06, 189.09, 189.11, 422, 383.1, 222/495, 496, 494, 491; 239/333
See application file for complete search history.

(56) References Cited

U.S. PATENT DOCUMENTS 2,342,288 A * 2/1944 Mai ............................... 222/384
2,717,178 A * 9/1955 Cornelius ...................... 239/333
(Continued)

FOREIGN PATENT DOCUMENTS

DE 103 30 040 A1 1/2005
DE 10 2006 024 563 A1 11/2007
(Continued)

OTHER PUBLICATIONS

"International Application Serial No. PCT/EP2009/001528, International Preliminary Report on Patentability mailed Feb. 12, 2010", 5 pgs.
(Continued)

*Primary Examiner* — Patrick M Buechner
(74) *Attorney, Agent, or Firm* — Schwegman Lundberg & Woessner, P.A.

(57) ABSTRACT

A metering device for metered dispensing of liquid preparations, in particular for metering medicinal, pharmaceutical and cosmetic liquid preparations, the use of preservatives being able to be dispensed with.

19 Claims, 8 Drawing Sheets

(52) U.S. Cl.
CPC ........ *B05B 11/0024* (2013.01); *B05B 11/0043* (2013.01); *B05B 11/0048* (2013.01); *B05B 11/3015* (2013.01); *B05B 11/3022* (2013.01); *B05B 11/3074* (2013.01); *B05B 11/3077* (2013.01)

(56) References Cited

U.S. PATENT DOCUMENTS

| | | | | |
|---|---|---|---|---|
| 3,545,682 | A | * | 12/1970 | Beard ........................... 239/469 |
| RE28,366 | E | * | 3/1975 | Pechstein ...................... 239/333 |
| 4,182,496 | A | * | 1/1980 | Burke ............................ 239/492 |
| 4,485,943 | A | * | 12/1984 | Czech ............................ 222/256 |
| 4,657,161 | A | * | 4/1987 | Endo et al. .................... 222/256 |
| 4,728,008 | A | * | 3/1988 | Graf et al. ................... 222/321.5 |
| 4,856,679 | A | * | 8/1989 | Czech ............................ 222/136 |
| 4,872,596 | A | * | 10/1989 | Corsette ........................ 222/380 |
| 4,890,773 | A | * | 1/1990 | Corsette ........................ 222/380 |
| 5,037,007 | A | * | 8/1991 | Deussen .................... 222/321.6 |
| 5,038,965 | A | * | 8/1991 | Cater ............................. 222/255 |
| 5,842,616 | A | * | 12/1998 | Ruscitti et al. ............. 222/321.3 |
| 6,082,592 | A | | 7/2000 | McKenna et al. |
| 6,302,304 | B1 | * | 10/2001 | Spencer ........................ 222/260 |
| 6,851,583 | B2 | * | 2/2005 | Masuzzo et al. ............ 222/321.6 |
| 7,249,693 | B2 | * | 7/2007 | Buxmann ................. 222/189.11 |
| 2003/0164385 | A1 | * | 9/2003 | Masuzzo et al. ............ 222/321.7 |
| 2004/0256414 | A1 | * | 12/2004 | Graf ............................ 222/321.1 |
| 2005/0173459 | A1 | * | 8/2005 | Buxmann ................... 222/321.6 |
| 2006/0255072 | A1 | * | 11/2006 | Hagin et al. ................. 222/321.7 |
| 2007/0151987 | A1 | * | 7/2007 | Arghyris et al. ............ 222/386.5 |

FOREIGN PATENT DOCUMENTS

| | | |
|---|---|---|
| EP | 0 473 892 A2 | 3/1992 |
| EP | 0 765 690 A1 | 4/1997 |
| EP | 1 327 478 A1 | 7/2003 |
| EP | 1 380 352 A1 | 1/2004 |

OTHER PUBLICATIONS

"International Application Serial No. PCT/EP2009/001528, International Search Report mailed Jun. 3, 2009", 8 pgs.

"International Application Serial No. PCT/EP2009/001528, Written Opinion mailed Jun. 3, 2009", 5 pgs.

"International Application No. PCT/EP2009/001528, Translation of International Preliminary Report on Patentability mailed Jan. 13, 2011", 7 pgs.

* cited by examiner

METERING DEVICE

PRIORITY CLAIM TO RELATED APPLICATIONS

This application is a national stage application under 35 U.S.C. §371 of PCT/EP2009/001528, filed Mar. 4, 2009, and published as WO 2009/109370 A1 on Sep. 11, 2009, which claims priority to German Application No. 10 2008 012 468.0, filed Mar. 4, 2008, and to German Application No. 10 2008 027 987.0, filed Jun. 12, 2008, which applications and publication are incorporated herein by reference and made a part hereof in their entirety, and the benefit of priority of each of which is claimed herein.

The present invention relates to a metering device for metered dispensing of liquid preparations, in particular for metering medicinal, pharmaceutical and cosmetic liquid preparations, the use of preservatives being able to be dispensed with. Further uses exist in the field of foodstuffs, e.g. for food supplements, spices, etc.

A metering device for dispensing germ-free fluid is known for example from EP 0 473 892 A2. The metering device portrayed herein is however constructed from very many individual parts, which makes both the production unnecessarily complicated and expensive and also makes the portrayed metering device unreliable and susceptible to faults.

Furthermore, with this already known metering device, sufficiently precise metering of the preparation to be metered is not possible in all cases.

Starting herefrom it is the object of the present invention to provide a metering device for metered dispensing of liquid preparations which has as simple a construction as possible and hence avoids the disadvantages known from the state of the art.

This object is achieved with the features of patent claim 1. The dependent claims thereby represent advantageous developments.

According to the invention, it is hence proposed to develop the metering device known from the state of the art such that a spring-operated outlet valve is disposed in the region of the end of the outlet channel, the spring of which is guided in a separate recess connected to the outlet channel.

Because of the arrangement of the outlet valve in the region of the end of the outlet channel, optimum metering of preparations to be metered is achieved under all operating conditions. In particular, it is advantageous with this solution that, when the metering device has been left to stand for a fairly long time, no drying-out of the liquid preparation situated in the outlet channel to the nozzle results, likewise contamination, for example by bacteria, of the liquid situated in the outlet channel is effectively prevented. The outlet valve according to the invention is thereby constructed such that a spring, i.e. a valve spring, is guided in a recess, advantageously a groove which is connected to the outlet channel and serves for operation of the outlet valve, i.e. the valve piston.

If now the metering device of the invention is activated, the liquid conveyed out of the interior of the metering device exerts a pressure against the valve spring and the valve piston so that the piston moves in the direction of the spring and releases the outlet opening, as a result of which the liquid can emerge. As a result of the fact that now the valve spring is guided in a separate recess, it is ensured in addition that the liquid preparation which is intended to be metered does not come in contact with the spring.

In the case of the metering device according to the invention, the nozzle and the outlet channel are guided out either laterally from the hollow body, which is configured preferably as a hollow cylinder, or else the nozzle is guided externally via the cap.

A further advantageous embodiment of the invention proposes that the outlet channel and/or the valve body have an agent acting as a bactericide. This can be effected such that the relevant parts are formed either directly from the agent acting as a bactericide, such as for example silver, or in that the corresponding regions have a coating acting as a bactericide. Likewise, the possibility is provided that inserts acting as a bactericide are present, this can be effected for example in the form of a spring or spiral in the region of the nozzle opening which has a bactericidal effect.

Silver or silver salts, such as e.g. silver chloride, are possible in particular as agents acting as a bactericide.

The metering device according to the invention is furthermore distinguished preferably in that it has a significantly simplified construction. As a result of the fact that the cap can be configured in one piece with the hollow body which is preferably cylindrical, the possibility is provided of producing the actuation body from a significantly reduced number of individual parts and hence of lowering the production costs. In particular, it is thereby preferred if not only the cap with the hollow cylinder but also again the pump piston is configured in one piece, i.e. monolithically. For example the above-mentioned individual parts can be produced economically in the injection moulding process from quasi any plastic materials. A further advantage resides in the fact that the packaging turns out to be substantially smaller with the same contents and the same functionality, which can be regarded as equally advantageous from economic and ecological aspects.

The outlet channel with the nozzle can be configured also as an integral component of the cap, the connection to the pump chamber, in this case, being configured preferably by a channel extending in the pump piston. As an alternative hereto, likewise a construction is possible in which the outlet channel with the nozzle is present as a separate component.

In an advantageous embodiment, the pump chamber is connected via an inlet opening to the storage container. In order to ensure effective continuous flowing of the liquid to be metered and also to prevent backflows of the liquid situated in the pump chamber during the metering process, this inlet opening has an inlet valve. This inlet valve can be configured for example as a spherical valve and can be formed in particular from substances or materials which act as a bactericide and are coated with materials which act as a bactericide, such as for example silver or silver chloride. A stainless steel ball coated with silver is hereby particularly preferred as inlet valve.

In order to ensure replenishment of the actuation body after the metering process and also refilling of liquid from the storage container into the pump chamber, a mechanical restoring device is disposed preferably between the pump chamber and the cap. This can be in particular a return spring and/or bellows, such as e.g. a return spring provided with bellows.

In the metering device according to the invention, it is favourable furthermore if the storage container has a friction-reduced finish on its inside. The inside is preferably fitted with a polyethylene layer. In this case, the storage container can be produced in a two-component injection moulding process. In addition to the inside of the storage container, the piston can also have a sliding layer at the same time and/or independently hereof. The coating with polyethylene described in this paragraph reduces not only the friction but it also offers the advantage of making it permissible possibly for medical purposes of use.

It is further preferred if the metering device operates without air equalisation, i.e. no pressure equalisation in the storage container by inflowing air is effected during actuation thereof.

The storage container can also have a piston, e.g. a drag piston. The base of the storage container can be equipped with a filter matrix, e.g. an activated carbon filter or a nylon or polyvinylidene fluoride membrane (PVDF) which ensures that e.g. bacteria and spores cannot pass through with the inflowing air.

The present invention is explained in more detail with reference to the subsequent Figures without being restricted to the special embodiments represented in the Figures.

There are thereby shown

FIG. 1 in an enlarged representation, the actuation body of the metering device according to the invention with a first embodiment of the outlet valve.

FIG. 2 likewise shows again in enlarged representation the actuation body of the metering device according to the invention, here with an outlet channel directed diagonally outwards.

FIG. 3 likewise shows in enlarged representation the actuation body of a metering device according to the invention, the outlet nozzle here being guided outwards via the cap.

FIG. 4 now shows in total view in FIG. 4a a metering device comprising an actuation body and a drag piston flask, FIG. 4a showing the empty state and FIG. 4b the filled state of the drag piston flask.

FIG. 6a thereby shows the full state of the metering device and FIG. 6b the emptied variant.

FIG. 7a shows the full state of the supply container and FIG. 7b the same metering device in the emptied state.

Figure 1:
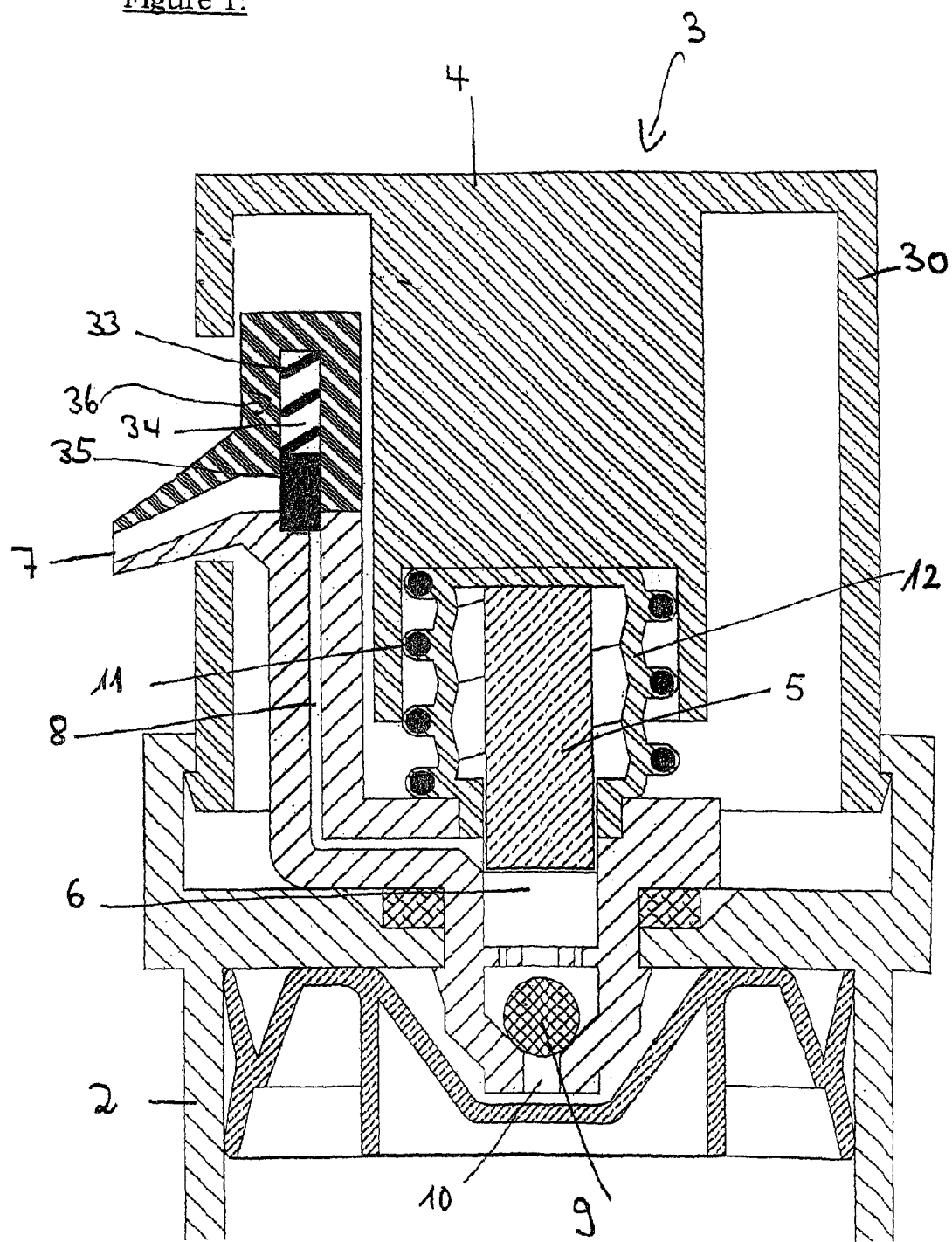

FIG. 1 now shows, in an enlarged representation, the actuation body 3 of the metering device 1 according to the invention. In FIG. 1, the storage container 2 is only indicated in the Figure. With reference to the configuration of the storage container, reference is made to FIGS. 4 to 7.

The actuation body 3 of the embodiment according to FIG. 1 thereby comprises a cap 4 and also a hollow body in cylindrical form 30 and a pump piston 5 which is connected, on one side, to the cap 4 and to the cylindrical hollow body 30 and can be introduced into the pump chamber 6 in a form fit. It is now essential that an outlet valve 36 which comprises a pressure spring 33 and a valve piston 35 is disposed in the region of the end of the outlet channel 8. The pressure spring 33 is thereby guided in a recess 34 which is connected to the outlet channel 8. By actuation of the cap 4 by the user pressing thereon, the pump piston 5 now moves into the pump chamber 6 and consequently displaces the liquid situated in the pump chamber 6 through the outlet channel 8 towards the nozzle 7. Because of the thereby resulting excess pressure, the outlet valve 36 is opened counter to the tensioning force of the spring 33 holding the valve 36 in the closed position so that discharge of the liquid is made possible. The stroke volume of the piston 5 thereby determines the dispensed metered quantity. After completion of the metering process, the cap 4 with connected piston 5 is guided back automatically into the starting position by the return spring 11 which is incorporated in bellows 12, a low pressure being produced in the pump chamber 6 so that liquid flows out of the storage container 2 into the pump chamber 6 through the opening 10 closed by the valve 9. The valve 36 can be formed from materials acting as a bactericide or with materials coated with a substance acting as a bactericide (e.g. silver or silver salts), just as the inlet valve 9 so that it is ensured that sterilise conditions of the contained liquid preparation are maintained efficiently. In the above-described embodiment, reference should be made in particular to the fact that, as a result of the fact that the outlet valve 36 is configured such that the spring 33 is guided in the recess 34, safe and sterile actuation of the outlet valve is possible since the liquid does not come in contact with the spring 33.

Figure 2:
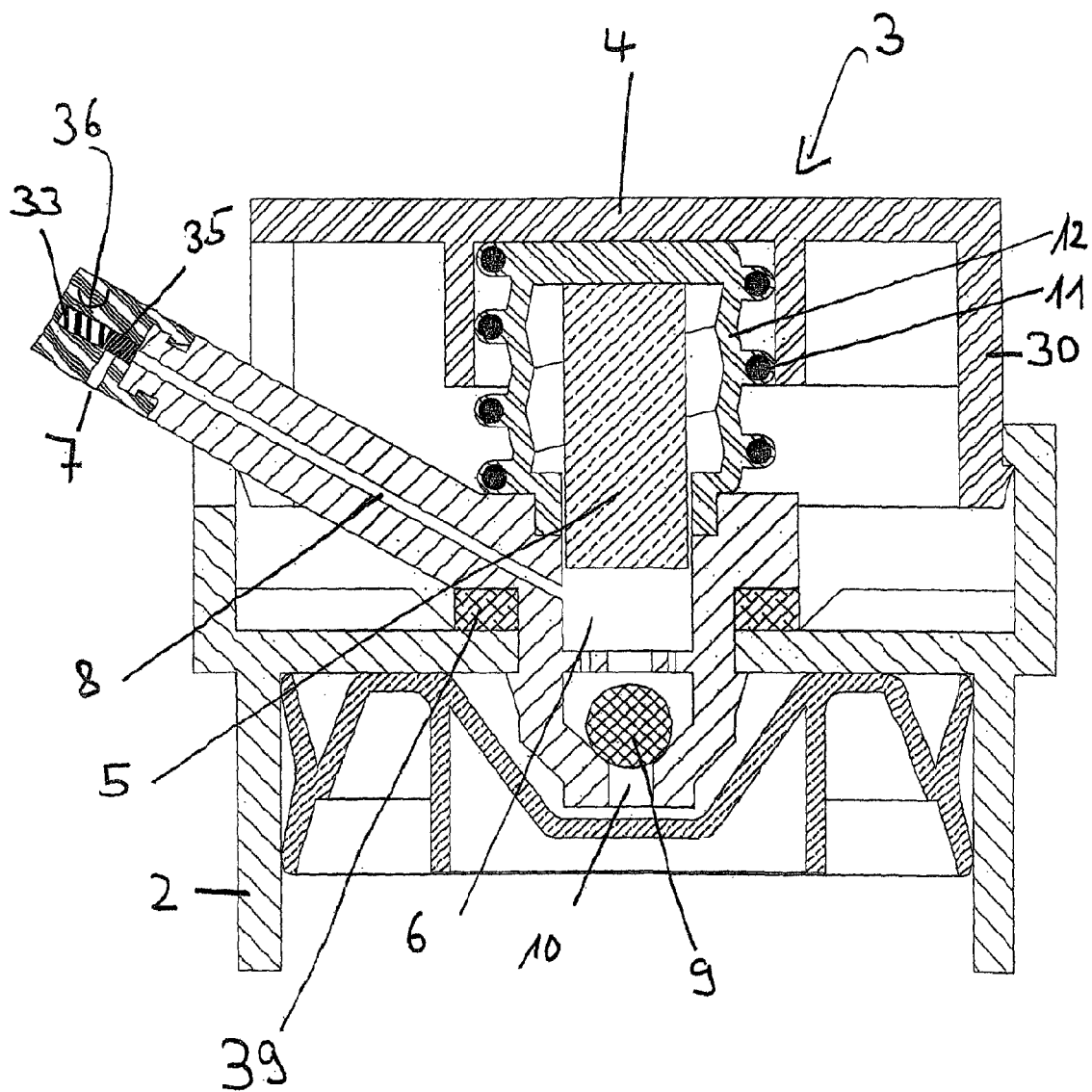

FIG. 2 shows a further optimised embodiment of the actuation body 3 which again is illustrated in an enlarged representation. In contrast to the embodiment as described in FIG. 1, in this embodiment according to FIG. 2 the outlet channel 8 is guided outwards in a straight line through the cylindrical hollow body 30, which represents a simplification from a manufacturing point of view. It is likewise ensured by this embodiment that the height of the cap 4 configured as actuation button can be reduced, which lets the actuation body 3 and hence in total the metering device 1 become more compact. A further feature of the actuation body represented in FIG. 2 can be seen in the fact that the outlet valve 36, which again comprises a valve spring 33 and a valve body 35, and also the outlet nozzle 7 is accommodated in a housing snapped on to the outlet channel 8. As a result of this mechanical connection which is easy to release, easy accessibility is provided for example in the case of a blockage of the valve so that the outlet valve 36 can be cleaned without great complexity. Reference should also be made at this point to the fact that the actuation body 3 of the metering device according to the invention, as also the embodiment previously described in FIG. 1, already has an additional sealing element 39 which serves to seal the actuation body 3 relative to the storage container 2.

Figure 3:
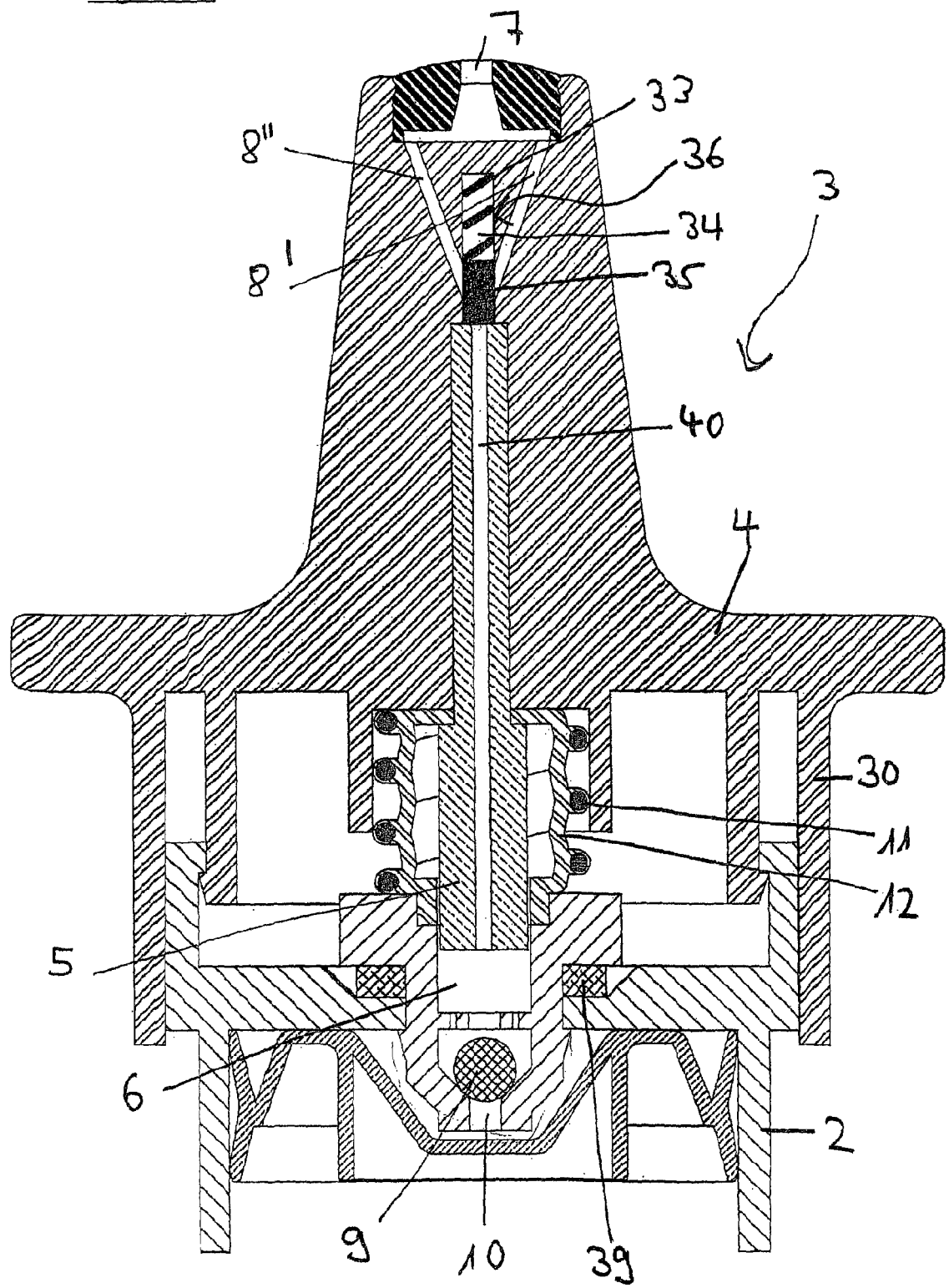

FIG. 3 shows again in enlarged representation a further embodiment of the actuation body 3 of the metering device according to the invention. The actuation body 3 of this embodiment is again constructed from a cap 4 which is connected monolithically to a cylindrical hollow body 3. In contrast to the embodiments according to FIGS. 1 and 2, the nozzle 7 here is now guided outwards via the cap 4. It is thereby merely required for production that a riser 40 is incorporated in the cap 4, the riser 40 with the two partial outlet channels 8' and 8" being connected to communicate via the valve 36. In this embodiment also, the valve 36 is constructed such that it comprises a spring 33 and a valve piston 35. Of course, the invention also comprises embodiments in which only one outlet channel 8' or also more than two outlet channels are provided. The further reference numbers correspond to those as were described already in FIGS. 1 and 2.

Figure 4:
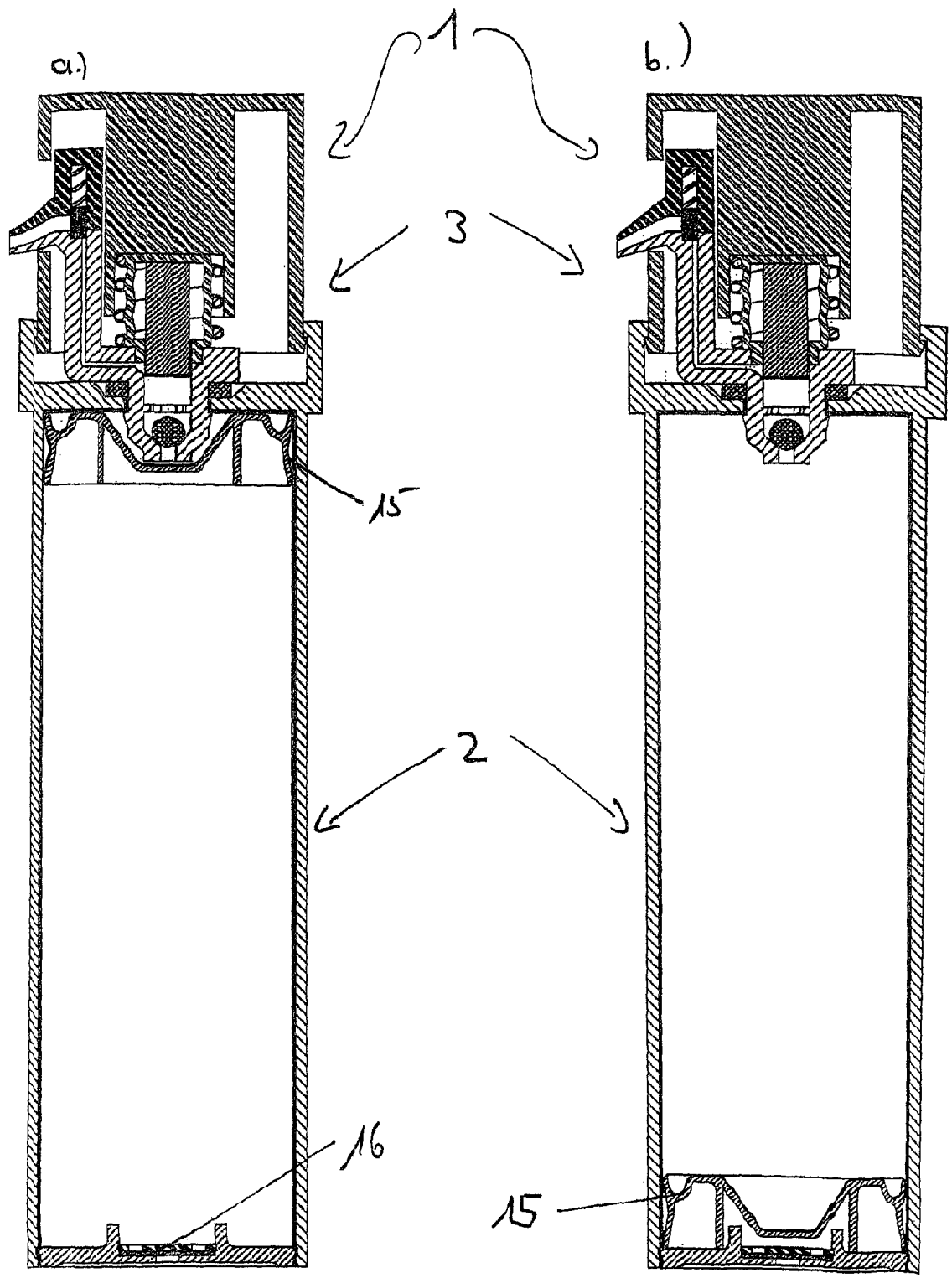

FIG. 4 now shows schematically in section the construction of a metering device 1 according to the invention comprising an actuation body 3 and a storage container 2. The construction of the actuation body 3 thereby corresponds to that as already described in detail in FIG. 1. The storage container 2 is thereby configured such that it has a piston 15 and a filter matrix 16. The filter matrix 16 can be accessible in addition via a base screw connection.

The actuation body 3 is connected to the storage container 2 via a plug-in connection in a toothed manner, the connection can however also be effected in any other way, e.g. by a screw connection. In FIG. 4a, the storage container 2 is now represented in the emptied state, i.e. the drag piston 15 is situated directly on the actuation body 3, whereas FIG. 4b shows the storage container 2 in the filled state, i.e. the drag piston 15 is disposed on the base. In the embodiment according to FIG. 4, which shows the simplest design of a drag piston flask, it can thereby also be provided that the inner surfaces of the storage container 2 are provided with an additional friction-reducing coating. The coating with polyethylene reduces not only the friction but it also offers the advantage of being permissible for medicinal purposes of use.

Figure 5:
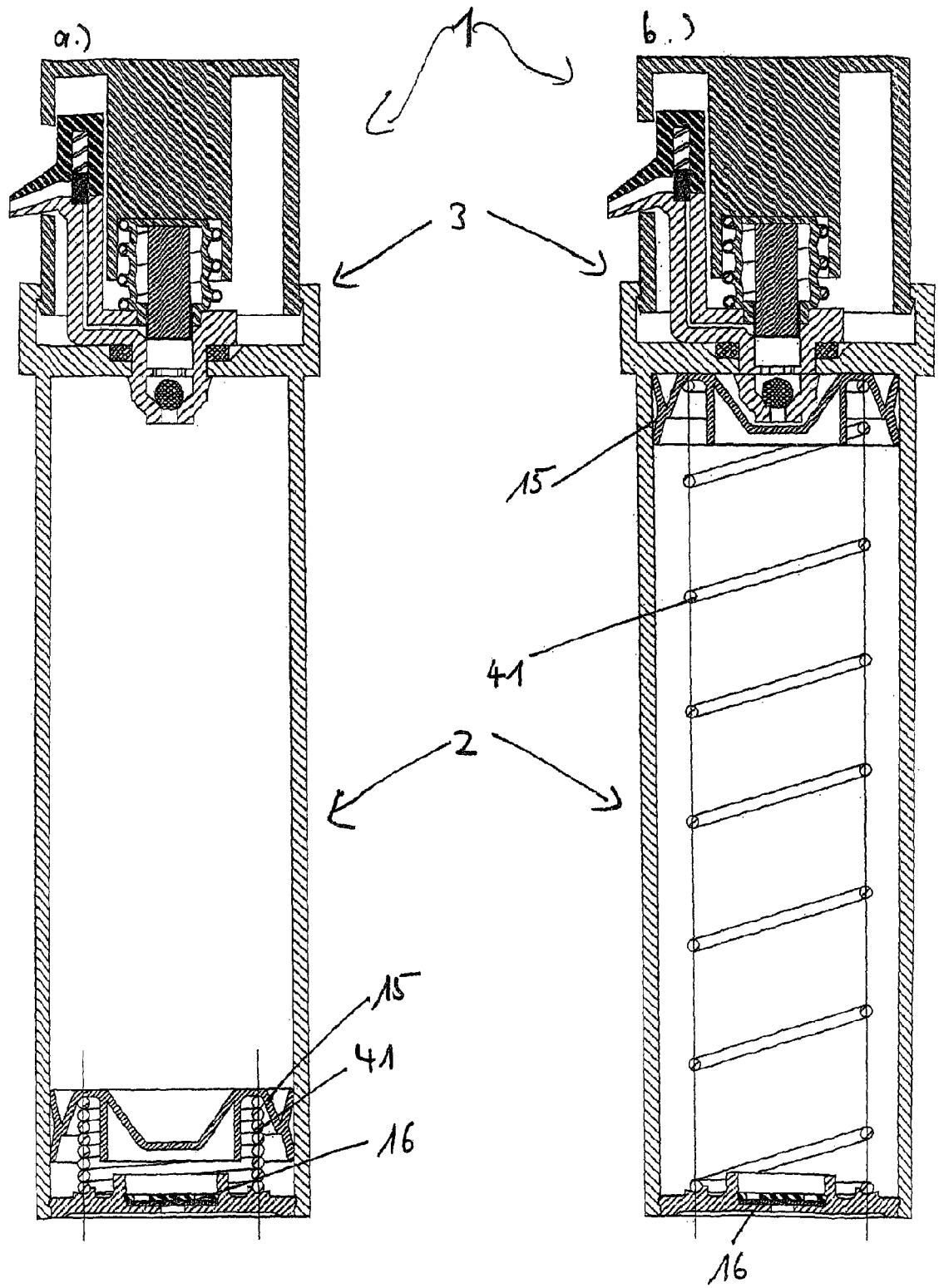
FIG. 5 shows, in a modification of FIGS. 4a and b in FIGS. 5a and 5b, a metering device with a drag piston flask with an additional pressure spring under the drag piston, FIG. 5a showing the filled state and FIG. 5b the empty state.

FIG. 5 now shows a further embodiment which corresponds to the one as described already in FIG. 4, however it is provided here in addition that a pressure spring 41 is disposed under the drag piston 15. FIG. 5a thereby shows the storage container 2 in the filled state and FIG. 5b the storage container 2 in the emptied state, the pressure spring 41 here then guiding the drag piston 15 upwards.

Figure 6:
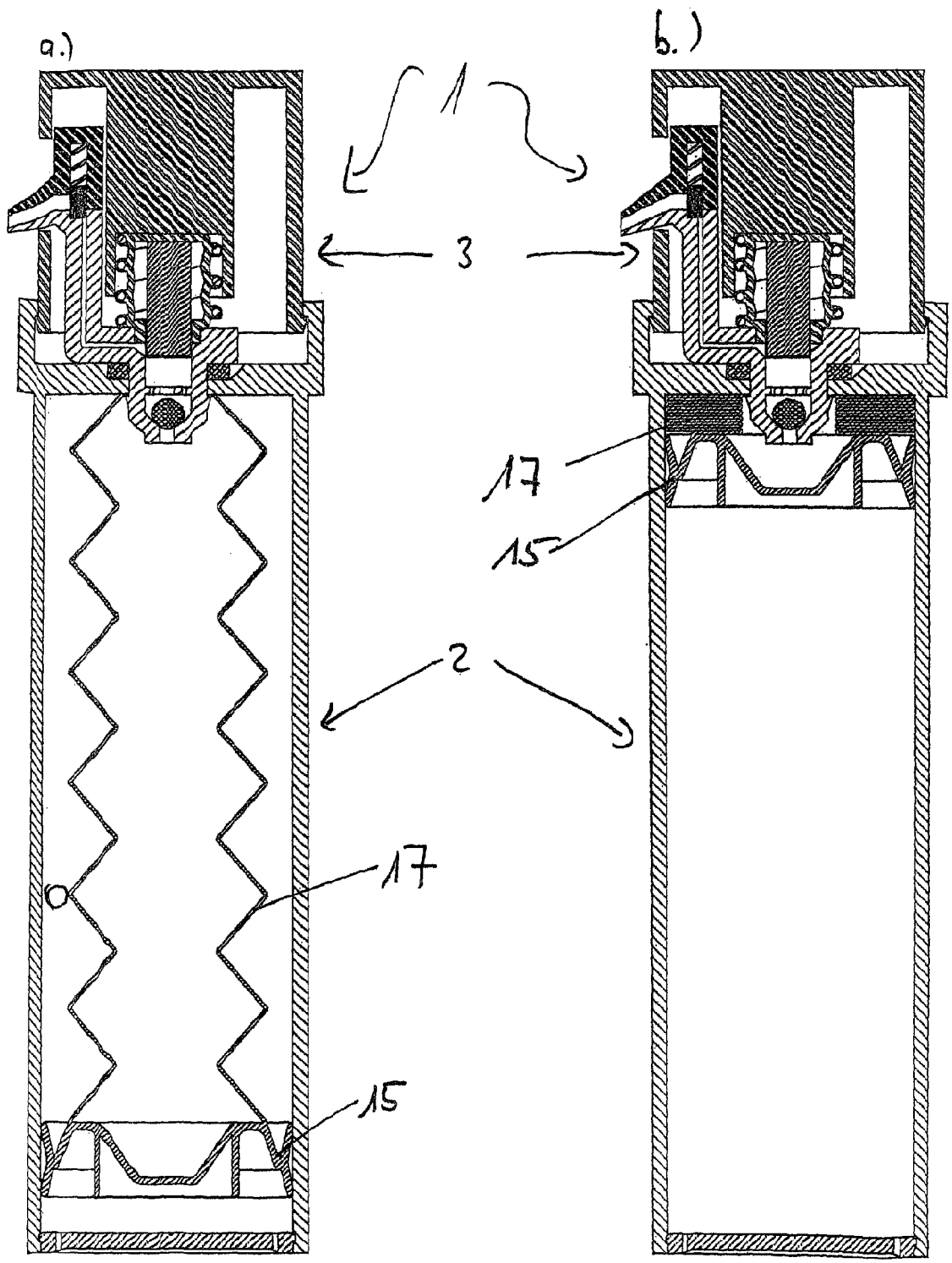
FIG. 6 shows a further embodiment of the metering device according to the invention, the storage container here being equipped with bellows.

FIG. 6 now shows a further embodiment, bellows 17 being provided here in the storage container 2. The bellows 17 thereby have a pretension, i.e. they are folded together in the emptied state (FIG. 6b). In FIG. 6a, the state is thereby represented when the storage container 2 is filled. In this case, the bellows 17 are then unfolded. In the embodiment represented in FIG. 6, in contrast to the embodiment according to FIG. 5, no additional filter device is provided on the base.

Figure 7:
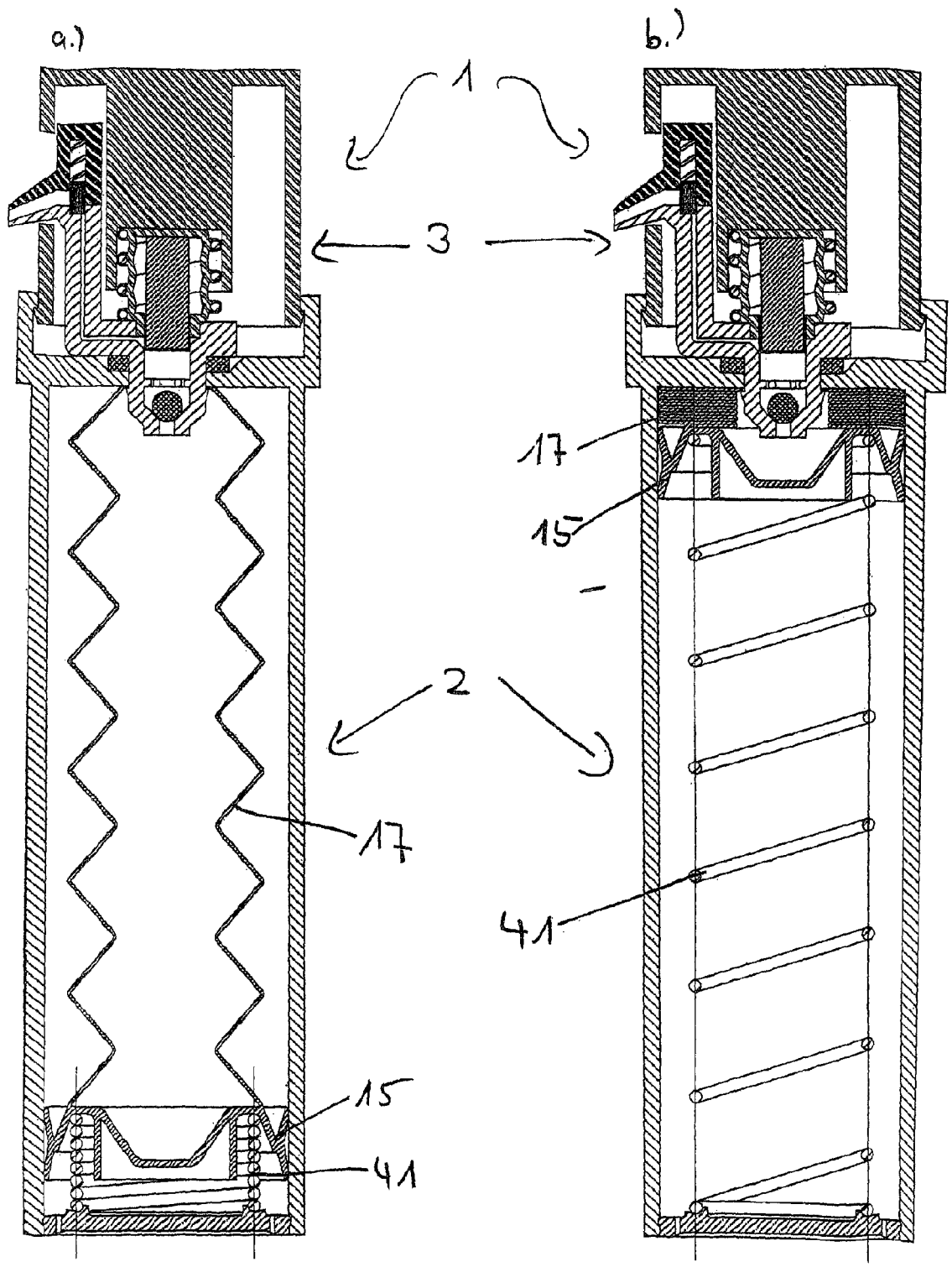
FIG. 7 shows a further embodiment, in a modification relative to FIG. 6, an additional pressure spring being provided here under the drag piston.

FIG. 7 finally shows a further embodiment which corresponds to the one described already in FIG. 6, however yet again an additional compression spring 41 is provided here under the drag piston 15. In this embodiment, an additional pressure spring 41 is hence disposed in addition to the bellows 17.

Figure 8:
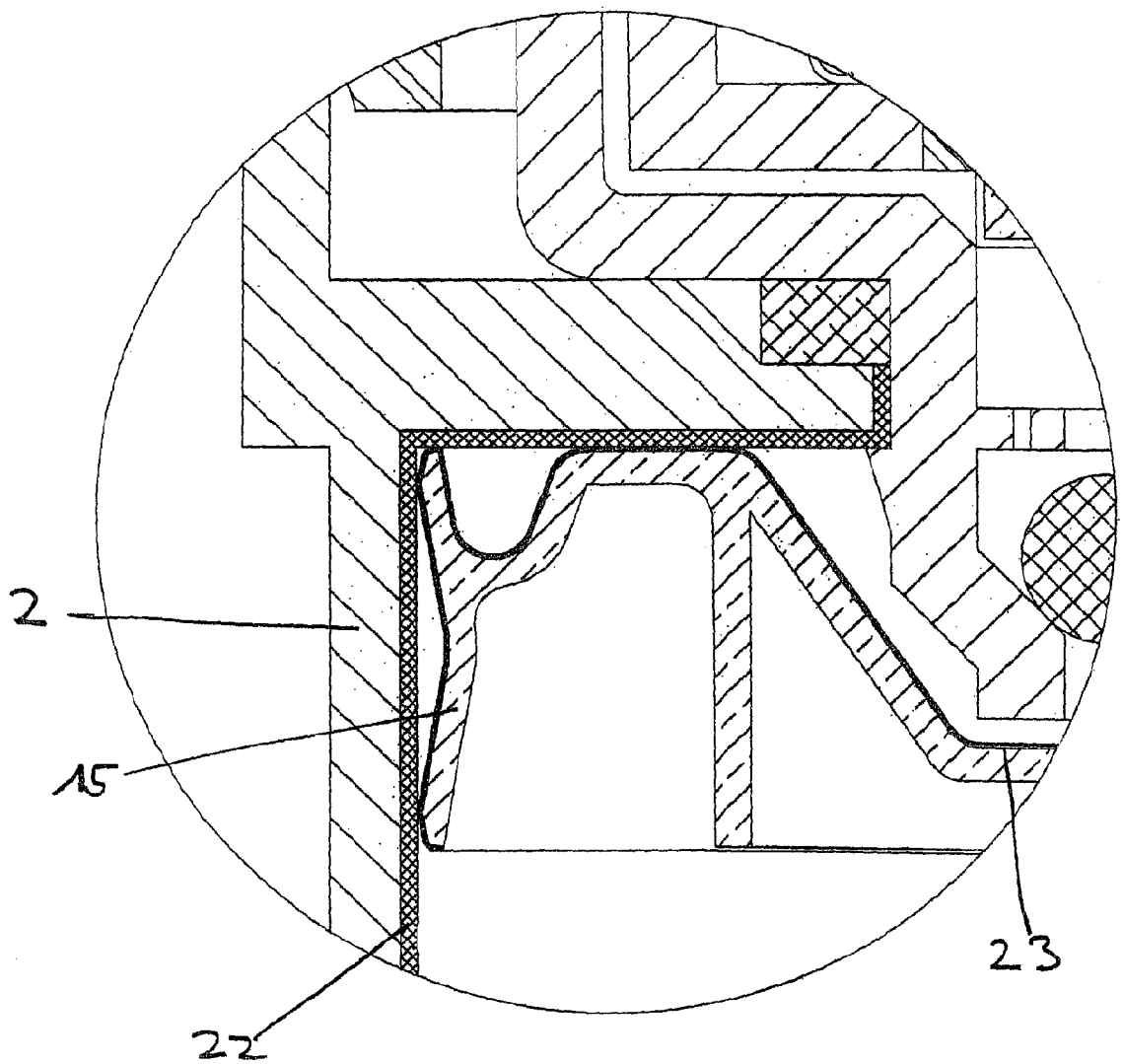
FIG. 8 shows, as a section in an enlarged representation, the configuration of a coated drag piston.

FIG. 8 now shows a section from the storage container according to FIG. 4, 5 or 6 or 7, in addition the drag piston 15 here being equipped on its side orientated towards the inner wall of the container 2 with a sliding layer, e.g. a polyethylene coating 23. Furthermore, the container inside 2 of the storage container has an additional sliding layer 22. The coating with polyethylene reduces not only the friction but it also offers the advantage of being permissible for medicinal purposes of use.

The invention claimed is:

1. A metering device for metered dispensing of a liquid preparation, the metering device comprising:
    a storage container for the liquid preparation and an actuation body which is capable of being connected to the storage container, the actuation body having a hollow body connected to a cap;
    a pump piston;
    a pump chamber; and
    a nozzle connected to the pump chamber via an outlet channel, wherein the nozzle is arranged to be capable of being guided out laterally from the hollow body,
    wherein a spring-operated outlet valve is disposed at a liquid output end of the metering device, the spring of which is guided in a separate recess that is isolated from the outlet channel by the valve such that the liquid preparation that is intended to be metered via the outlet channel does not come in contact with the spring.

2. The metering device according to claim 1, wherein the nozzle is arranged to be capable of being guided out via the cap.

3. The metering device according to claim 1, wherein the nozzle connected to the outlet channel is configured as a separate component.

4. The metering device according to claim 1, wherein the outlet valve is disposed directly at the liquid output end of the outlet channel.

5. The metering device according to claim 1, wherein the hollow body connected to the cap is cylindrical.

6. The metering device according to claim 1, wherein the pump chamber is connected via an inlet opening provided with an inlet valve to the storage container.

7. The metering device according to claim 1, wherein the outlet channel and/or the valve body of the outlet valve has an agent capable of acting as a bactericide, wherein the agent capable of acting as a bactericide is silver or a silver salt, and
    wherein the agent capable of acting as a bactericide includes silver chloride.

8. The metering device according to claim 1, wherein the cap and the hollow body are configured in one piece.

9. The metering device according to claim 8, wherein the cap, the hollow body and the pump piston are configured in one piece.

10. The metering device according to claim 1, wherein the outlet channel and/or the valve body of the outlet valve has an agent capable of acting as a bactericide.

11. The metering device according to claim 10, wherein the agent capable of acting as a bactericide includes at least one of a coating or an insert.

12. The metering device according to claim 10, wherein the agent capable of acting as a bactericide is silver or a silver salt.

13. A metering device for metered dispensing of a liquid preparation, the metering device comprising:
    a storage container for the liquid preparation and an actuation body which is capable of being connected to the storage container, the actuation body having a hollow body connected to a cap;
    a pump piston;
    a pump chamber; and
    a nozzle connected to the pump chamber via an outlet channel,
    wherein a spring-operated outlet valve is disposed at a liquid output end of the metering device, the spring of which is guided in a separate recess that is isolated from the outlet channel by the valve such that the liquid preparation that is intended to be metered via the outlet channel does not come in contact with the spring; and
    wherein a mechanical restoring device for restoring the cap is disposed between the pump chamber and the cap.

14. The metering device according to claim 13 wherein the mechanical restoring device comprises a return spring and/or bellows.

15. A metering device for metered dispensing of a liquid preparation, the metering device comprising:
    a storage container for the liquid preparation and an actuation body which is capable of being connected to the storage container, the actuation body having a hollow body connected to a cap;
    a pump piston;
    a pump chamber; and
    a nozzle connected to the pump chamber via an outlet channel,
    wherein a spring-operated outlet valve is disposed at a liquid output end of the metering device, the spring of which is guided in a separate recess that is isolated from the outlet channel by the valve such that the liquid preparation that is intended to be metered via the outlet channel does not come in contact with the spring; and
    wherein the metering device is configured to operate free of air equalization.

16. A metering device for metered dispensing of a liquid preparation, the metering device comprising:

a storage container for the liquid preparation and an actuation body which is capable of being connected to the storage container, the actuation body having a hollow body connected to a cap;
a pump piston;
a pump chamber; and
a nozzle connected to the pump chamber via an outlet channel,
wherein a spring-operated outlet valve is disposed at a liquid output end of the metering device, the spring of which is guided in a separate recess that is isolated from the outlet channel by the valve such that the liquid preparation that is intended to be metered via the outlet channel does not come in contact with the spring; and
wherein the storage container has a piston and a filter matrix.

17. A metering device for metered dispensing of a liquid preparation, the metering device comprising:
a storage container for the liquid preparation and an actuation body which is capable of being connected to the storage container, the actuation body having a hollow body connected to a cap;
a pump piston;
a pump chamber; and
a nozzle connected to the pump chamber via an outlet channel,
wherein a spring-operated outlet valve is disposed at a liquid output end of the metering device, the spring of which is guided in a separate recess that is isolated from the outlet channel by the valve such that the liquid preparation that is intended to be metered via the outlet channel does not come in contact with the spring; and
wherein the storage container has a friction-reducing finish on the inside.

18. A metering device for metered dispensing of a liquid preparation, the metering device comprising:
a storage container for the liquid preparation and an actuation body which is capable of being connected to the storage container, the actuation body having a hollow body connected to a cap;
a pump piston;
a pump chamber; and
a nozzle connected to the pump chamber via an outlet channel,
wherein a spring-operated outlet valve is disposed at a liquid output end of the metering device, the spring of which is guided in a separate recess that is isolated from the outlet channel by the valve such that the liquid preparation that is intended to be metered via the outlet channel does not come in contact with the spring; and
wherein the piston, on its side orientated towards the inside of the storage container, has a friction-reducing finish.

19. A metering device for metered dispensing of a liquid preparation, the metering device comprising:
a storage container for the liquid preparation and an actuation body that is capable of being connected to the storage container, the actuation body having a cylindrical hollow body connected to a cap;
a pump piston;
a pump chamber;
a mechanical restoring device, disposed between the pump chamber and the cap, for restoring the cap; and
a nozzle, capable of being guided out laterally from the hollow body via the cap, the nozzle connected to the pump chamber via an outlet channel,
wherein a spring-operated outlet valve is disposed at a liquid output end of the metering device, the spring of which is guided in a separate recess that is isolated from the outlet channel by the valve such that the liquid preparation that is intended to be metered via the outlet channel does not come in contact with the spring.

* * * * *